(12) United States Patent
Im et al.

(10) Patent No.: US 7,357,144 B2
(45) Date of Patent: Apr. 15, 2008

(54) CONTAMINATION CONTROL APPARATUS, MANAGEMENT SYSTEM AND RELATED METHODS

(75) Inventors: Suk-Hee Im, Gyeonggi-do (KR); Chang-Su Lim, Gyeonggi-do (KR); Sun-Wook Park, Gyeonggi-do (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 512 days.

(21) Appl. No.: 11/018,837

(22) Filed: Dec. 21, 2004

(65) Prior Publication Data
US 2005/0145012 A1 Jul. 7, 2005

(30) Foreign Application Priority Data
Jan. 5, 2004 (KR) ............... 10-2004-0000229

(51) Int. Cl.
*G01N 19/10* (2006.01)
*B01D 46/00* (2006.01)

(52) U.S. Cl. ............ 137/15.04; 137/312; 137/240; 137/382; 73/31.03; 73/863; 96/413

(58) Field of Classification Search ........... 137/312, 137/240, 375, 382, 15.04, 15.01; 73/863; 73/31.03; 96/413
See application file for complete search history.

(56) References Cited

U.S. PATENT DOCUMENTS

| 4,253,684 A | 3/1981 | Tolbert et al. |
| 5,577,528 A * | 11/1996 | Saha et al. ............ 137/240 |
| 6,129,107 A * | 10/2000 | Jackson ............... 137/312 |
| 6,498,898 B2 | 12/2002 | Schmitt ............... 392/466 |
| 6,708,717 B1 * | 3/2004 | Coogle ............... 137/240 |
| 7,011,102 B2 * | 3/2006 | Folkers ............... 137/312 |

FOREIGN PATENT DOCUMENTS

| DE | 32 13 821 | 10/1983 |
| JP | 2000150387 | 5/2000 |
| KR | 1020020096608 | 12/2002 |

OTHER PUBLICATIONS

Translation of an Office Action as Issued by the German Patent and Trademark Office, dated Apr. 20, 2006.

* cited by examiner

Primary Examiner—Kevin Lee
(74) Attorney, Agent, or Firm—Myers Bigel Sibley & Sajovec

(57) ABSTRACT

A contamination control apparatus includes at least two pipes connected by a joint portion and configured to allow a processing fluid to flow therethrough, and a cover configured to enclose the joint portion and to provide an enclosed cavity between the cover and the joint portion. An inlet port is connected to the cover and configured to supply a gas to the cavity. An outlet port is connected to the cover and configured to exhaust the gas and a contaminant from the cavity.

25 Claims, 5 Drawing Sheets

CONTAMINATION CONTROL APPARATUS, MANAGEMENT SYSTEM AND RELATED METHODS

CROSS-REFERENCE OF RELATED APPLICATIONS

This application claims priority from Korean Patent Application No. 2004-229, filed on Jan. 5, 2004, the disclosure of which is incorporated herein by reference in its entirety.

FIELD OF THE INVENTION

The present invention relates to a contamination control apparatus, and more particularly, to a contamination control apparatus for reducing contaminants due to a leaked gas in a clean room.

BACKGROUND OF THE INVENTION

Semiconductor devices are generally manufactured by various fabrication (FAB) processes that form an electric circuit on a semiconductor substrate, such as a silicon wafer. An electrical die sorting (EDS) process can be used to inspect the electrical characteristics of the electric circuit, and a packaging process can be used to separate the semiconductor substrate into individual semiconductor chips and to seal each of the semiconductor chips using an epoxy resin. Examples of FAB processes that may be used include deposition processes for forming a thin layer on the semiconductor substrate, chemical mechanical polishing (CMP) processes that polish the thin layer, photolithography processes that form a photoresist pattern on the thin layer, etching processes that etch the thin layer into an electrical pattern using the photoresist pattern as a mask, ion implantation processes that implant ions into a predetermined region of the semiconductor substrate, cleaning processes for cleaning impurities from the semiconductor substrate, and inspection processes for inspecting a surface of the semiconductor substrate so as to detect defects in the thin layer or pattern.

The above FAB processes may be performed in a clean room to which clean air is supplied. A clean room generally includes a plurality of fan filter units, a fluid supply system and a utility zone. For example, a fan filter unit can be disposed on a top portion of the clean room and can supply the clean air into the clean room from a ceiling chamber thereof. The fluid supply system can be disposed on a bottom portion of the clean room to supply various processing fluids into the clean room. A pressure controller can be disposed in the utility zone. The pressure controller controls an inner pressure of the clean room and/or the inner pressures of various unit devices that perform the above FAB processes. The clean air can be supplied into the clean room through the fan filter unit, and the clean air can be discharged into the utility zone through a bottom panel of the clean room. Accordingly, the clean air circulates through an air circulation duct connecting the ceiling chamber and the utility zone.

Examples of processing fluids include various processing gases and chemicals used for manufacturing semiconductor devices known to those of skill in the art. The fluid supply system of a clean room can include a plurality of pipes through which the various processing fluids flow and a plurality of joints for connecting the pipes to each other. The joints can include one or more valves that control the pressure and amount of the processing fluid flowing therethrough.

Processing fluid may be leaked from the joint of the fluid supply system, and the leaked fluid can circulate in the clean room through the air circulation duct that connects the ceiling chamber and the utility zone. The circulating leaked fluid can contaminate the operating environment in the clean room.

SUMMARY OF THE INVENTION

According to embodiments of the present invention, a contamination control apparatus includes at least two pipes connected by a joint portion and configured to allow a processing fluid to flow therethrough, and a cover configured to enclose the joint portion and to provide an enclosed cavity between the cover and the joint portion. An inlet port is connected to the cover and configured to supply a gas to the cavity. An outlet port is connected to the cover and configured to exhaust the gas and a contaminant from the cavity.

According to further embodiments of the present invention, a contamination management system includes at least one control unit that includes a cover configured to enclose a joint portion connecting at least two pipes and configured to allow a processing fluid to flow therethrough. The cover provides an enclosed cavity between the cover and the joint portion. An inlet port is connected to the cover and configured to supply a gas to the cavity. An outlet port is connected to the cover and configured to exhaust the gas and a contaminant from the cavity through a discharging duct. A plurality of sampling pipes are connected to the outlet port and configured to sample the contaminant. The sampling pipes are connected to a connection pipe connecting the outlet port and the discharging duct. An analyzing unit is connected to the sampling pipes and configured to analyze the sampled contaminant.

Methods for reducing contamination in a clean room according to embodiments of the present invention include enclosing a joint portion connecting at least two pipes with a cover that defines an enclosed cavity therebetween. A contaminant from the joint portion is contained in the cavity. A gas is supplied to the cavity through an inlet port. A gas mixture of the gas and the contaminant from the cavity is exhausted through an outlet port. In some embodiments, the exhausted gas mixture is analyzed.

DETAILED DESCRIPTION OF EMBODIMENTS OF THE INVENTION

Figure 1:
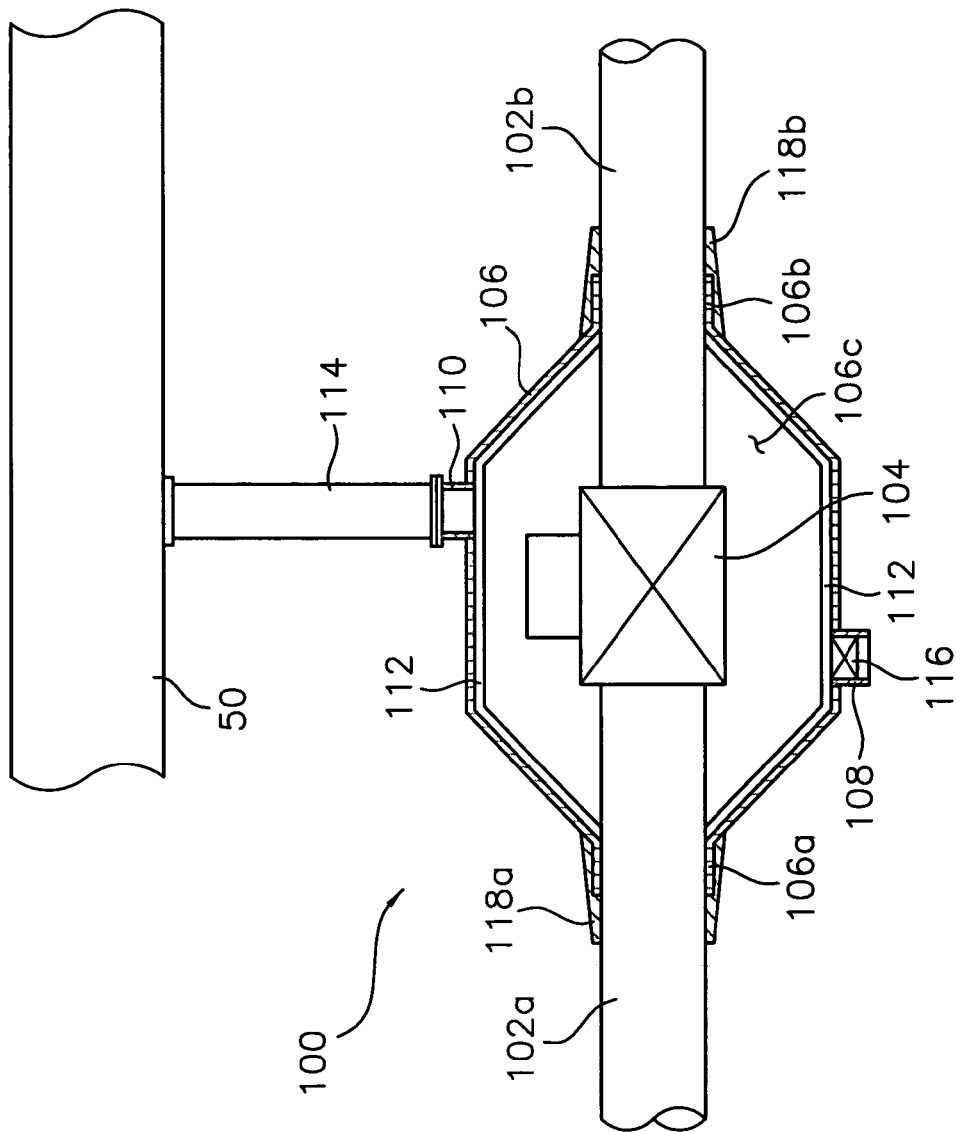
FIG. 1 is cross-sectional view of a contamination control apparatus according to embodiments of the present invention.

The present invention now will be described more fully hereinafter with reference to the accompanying drawings, in which embodiments of the invention are shown. Embodiments of the invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, the dimensions of elements may be exaggerated for clarity. Like numbers refer to like elements throughout. It will be understood that when an element is referred to as being "on" or "connected to" another element, it can be directly on or connected to the other element or intervening elements may also be present. In contrast, when an element is referred to as being "directly on" or "directly connected to" another element, there are no intervening elements present.

Figure 2:
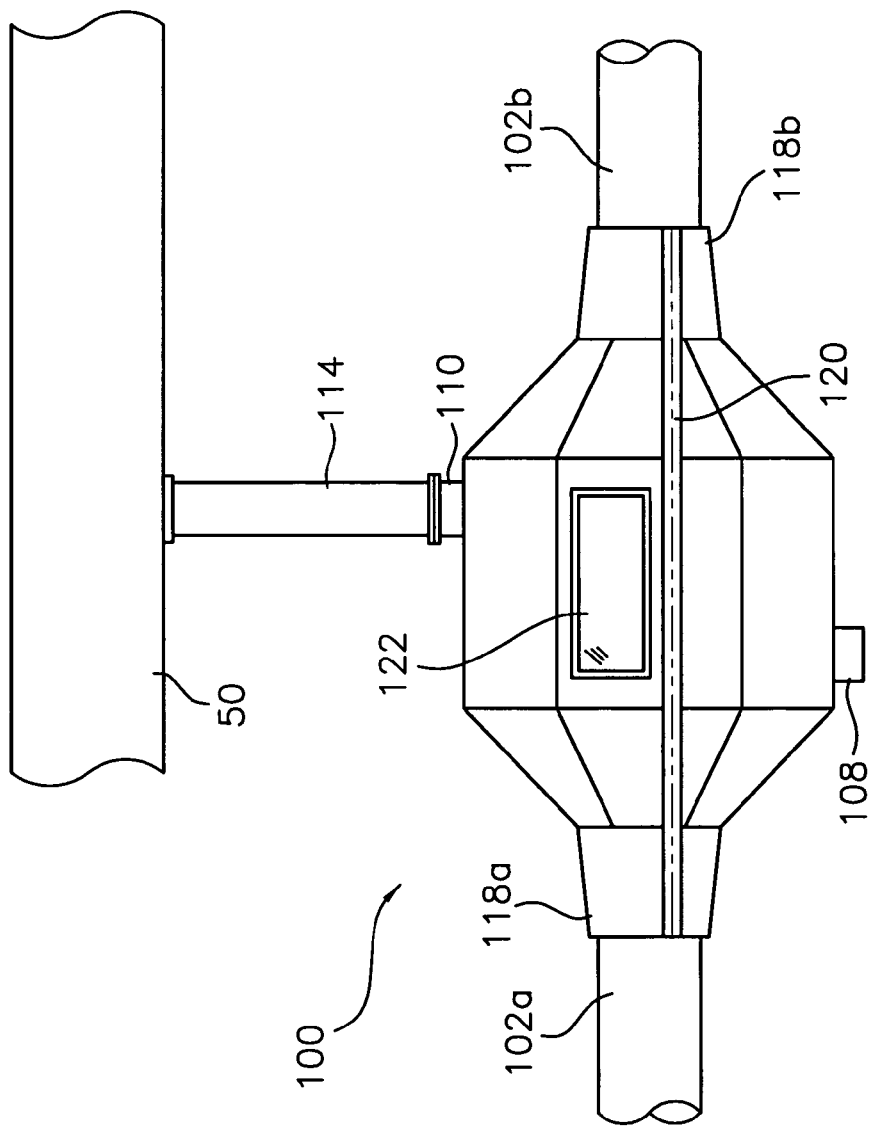
FIG. 2 is a front perspective view of the contamination control apparatus shown in FIG. 1.

Referring to FIGS. 1 and 2, a contamination control apparatus 100 includes a cover 106 configured to enclose or shield a joint portion 104. The joint portion 104 connects at least two pipes 102a and 102b through which a processing fluid flows. In this configuration, the spread of a contaminant that is leaked from the joint portion 104 may be reduced.

More specifically, the cover 106 defines a cavity 106c between the cover 106 and the joint portion 104 and/or pipes 102a and 102b. The cavity 106c is defined by the inner surface of the cover 106 and the outer surface of the joint portion 104 and the pipes 102a and 102b. The cover 106 includes an inlet port 108 and an outlet port 110 defined therein. The inlet port 108 is configured to supply a gas, such as the air, to the cavity 106c. The outlet port 110 is connected to a discharging duct 50 and is configured to discharge a mixture of the supplied gas and the contaminant through the discharging duct 50.

The cover 106 includes a first end portion 106a that covers the first pipe 102a, and a second end portion 106b that covers the second pipe 102b. The cover 106 is supported by a plurality of ribs 112, so that the cover 106 is substantially prevented from being deformed in shape. Accordingly, the cavity 106c has a generally constant size and shape because the shape and size of the cover 106 are substantially constant.

As illustrated, the outlet port 110 and the discharging duct 50 are connected to each other via a connection pipe 114. A mixture of the gas that is supplied into the cavity 106c of the cover 106 through the inlet port 108 and the leaked contaminant from the joint portion 104 flows into the discharging duct 50 via the connection pipe 114.

The connection pipe 114 can be used to connect the discharging duct 50 to various manufacturing processing devices (not shown) in which a process can be performed on an object, such as a silicon wafer or a glass substrate, using the processing fluid. In addition, the discharging duct 50 can be connected with a gas scrubber system (not shown) for purifying the gas that is discharged from the processing devices.

For example, a discharge gas that is discharged from a processing device can flow into the gas scrubber system via the discharging duct 50. The discharge gas can then be exhausted to the surrounding environment, such as into a clean room, after being purified in the gas scrubber system.

Accordingly, the cover 106 may reduce the spreading of any leaked contaminant from the joint portion 104. A gas mixture containing the contaminant can be exhausted into the surrounding environment (such as a clean room) through the connection pipe 114, the discharging duct 50 and a gas scrubber system. As a result, the contamination of an operating environment, such as a clean room for manufacturing a semiconductor device, may be reduced.

In some embodiments, the inlet port 108 includes a filter 116 configured to filter particles in the air supplied into the cavity 106c of the cover 106. Examples of the filter 116 include a high efficiency particulate air (HEPA) filter, an ultra low penetration air (ULPA) filter, etc.

The cover 106 may have excellent corrosion and chemical resistance with respect to the processing fluid. The cover 106 can include a flexible material, such as a fluoropolymer resin. An example of a fluoropolymer resin is a polytetrafluoroethylene (PTFE) resin (product of Dupont Co., Ltd, under the trade name TEFLON™).

The joint portion 104 connects the first and second pipes 102a and 102b, and can have at least one valve for controlling an amount or a pressure of the processing fluid flowing through the pipes 102a and 102b. Although embodiments of the present invention are described herein with reference to the joint portion 104 connecting the first and second pipes 102a and 102b with each other, it should be understood that the joint portion 104 can include a valve assembly configured to control the fluid amount between three or more pipes. Various fitting members for connecting numerous pipes and other configurations known to one of skill in the art may also be utilized in place of or in conjunction with the joint portion 104.

As illustrated, the contamination control apparatus 100 includes a pair of sealing pads 118a and 118b configured to seal the cover 106 at both end portions 106a and 106b thereof. Specifically, the first sealing pad 118a tightly adheres the first end portion 106a of the cover 106 to the first pipe 102a, and the second sealing pad 118b tightly adheres the second end portion 106b of the cover 106 to the second pipe 102b. Accordingly, the first sealing pad 118a seals the cover 106 at the first end portion 106a thereof, and the second sealing pad 118b seals the cover 106 at the second end portion 106b thereof, so that the cavity 106c is isolated from the surrounding environment. According to embodiments of the present invention, any suitable sealing material can be used for the sealing pads 118a and 118b. In particular, the sealing pads 118a and 118b may include a silicon-based material such as a silicone polymer.

In addition, with reference to FIG. 2, the contamination control apparatus 100 may further include a slide zipper 120 and a transparent window on the cover 106. The slide zipper 120 is configured to open and/or close the cover 106 when the cover 106 is installed around the joint portion 104. The transparent window 122 is configured to permit a user to view the inside of the cover 106. For example, if the processing fluid includes liquefied chemicals, an operator may view the leakage of the chemicals from the joint portion 104 through the transparent window 122.

Figure 3:
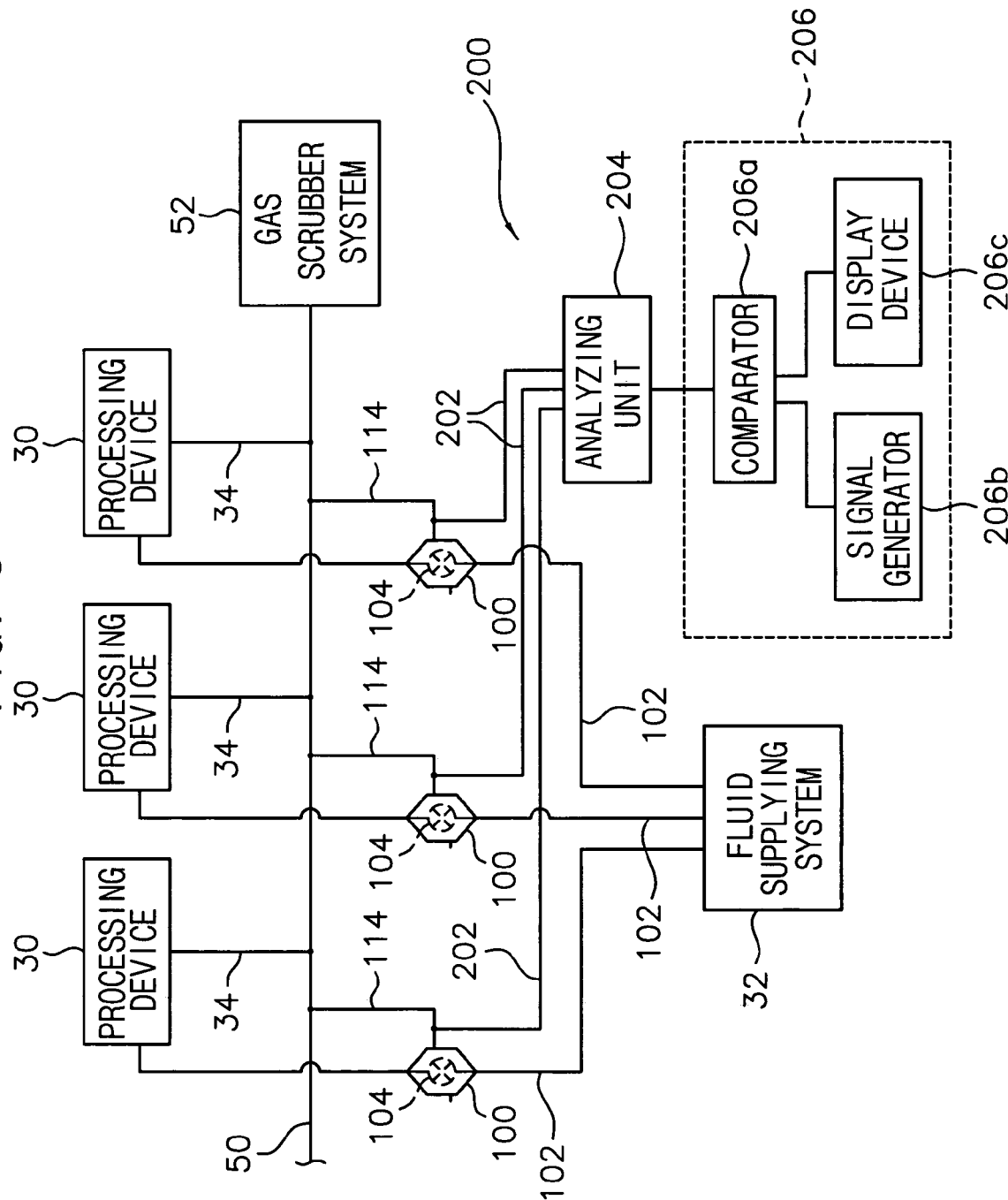
FIG. 3 is a block diagram illustrating a contamination management system according to embodiments of the present invention using the contamination control apparatus shown in FIG. 1.
Figure 4:
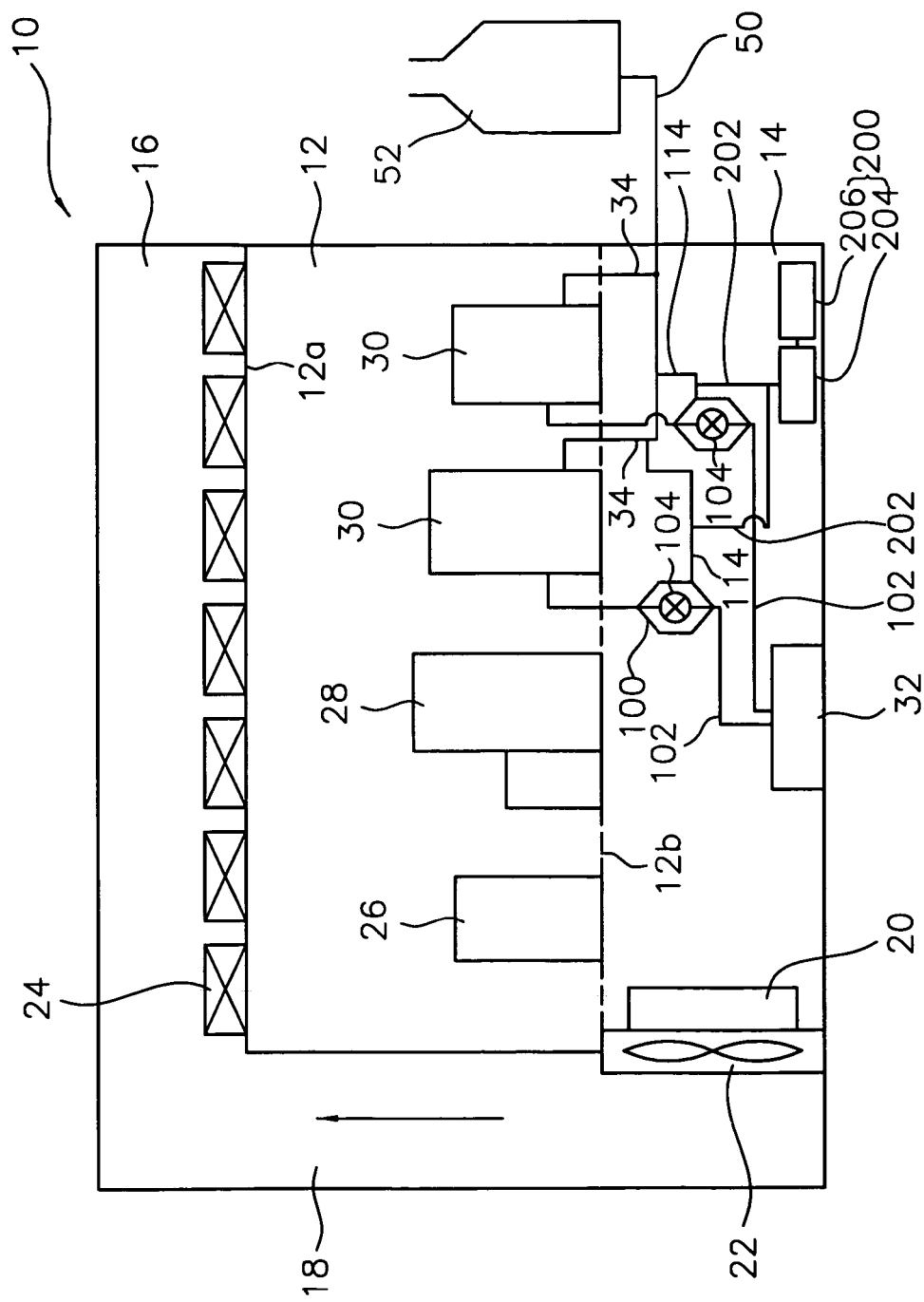
FIG. 4 is a schematic diagram of a clean room using the contamination management system shown in FIG. 3.

Referring to FIGS. 3 and 4, a contaminant management system 200 includes a plurality of control units (such as the contamination control apparatus 100 as described above with respect to FIGS. 1 and 2 and configured to reduce a contaminant that is leaked from the joint portion 104), a plurality of sampling pipes 202 configured to sample the contaminant, and an analyzing unit 204 configured to analyze the sampled contaminant.

As illustrated in FIG. 4, the contamination management system 200 may be installed in a clean room system 10 in which a manufacturing process for a semiconductor device is performed. As shown in FIG. 4, the clean room system 10 includes a clean room 12 in which various processes are performed on a semiconductor substrate, a utility zone 14 below the clean room 12, a ceiling chamber 16 above the clean room 12, an air circulation duct 18 through which the utility zone 14 and the ceiling chamber 16 are connected to each other, a cooling coil 20 for controlling a temperature of the air in the utility zone 14 and a circulation fan 22 for circulating the air in the utility zone 14. The clean room has a top panel 12a and a bottom panel 12b.

A plurality of fan filter units 24 is installed on the top panel 12a of the clean room 12 for supplying clean air into the clean room 12. A plurality of apertures can be formed in the bottom panel 12b of the clean room 12 so that the air in the clean room 12 can move to the utility zone 14. The air in the clean room 12 flows into the utility zone 14 through the penetration apertures in the bottom panel 12b, and the air in the utility zone 14 flows into the air circulation duct 18. The air in the air circulation duct 18 is supplied into the clean room 12 through the fan filter units 24. Therefore, the air in the clean room system 10 circulates through the air circulation duct 18.

The clean room 12 includes a transfer device 26 configured to transfer the semiconductor device, a storing device 28 for storing the semiconductor device, and a processing device 30 in which a predetermined manufacturing process is performed on the semiconductor substrate. For example, the processing device 30 may be connected with a fluid supply system 32, a vacuum system (not shown) and a power supplying system (not shown) in the utility zone 14.

The fluid supply system 32 includes a plurality of pipes 102 connected by joint portions 104, each of which are enclosed by a contamination control apparatus 100. The joint portions 104 include valves and may be positioned in the clean room 12 and/or the utility zone 14. The storing unit 28 may be installed in the utility zone 14 or outside of the clean room system 10. The fluid supply system 32 supplies various source gases, purge gases, inert gases used as a cooling gas or various chemicals into the processing devices 30.

Examples of the processing devices 30 include a deposition device for forming a thin layer on the semiconductor substrate, a photolithography device for forming a photoresist pattern on the thin layer, an etching device for transforming the thin layer into a pattern having predetermined electrical characteristics using the photoresist pattern as an etching mask, an ion implanting device for implanting ions onto a surface portion of the thin layer, a cleaning device for removing impurities from the pattern or the thin layer, and the like.

Each of the fan filter units 24 includes a high efficiency particulate air (HEPA) filter and/or an ultra low penetration air (ULPA) filter for removing particles from the circulated air, and/or a chemical filter for removing chemical impurities from the circulated air.

The processing devices 30 are connected to a gas scrubber system 52 outside of the clean room system 10 via the discharging duct 50. The byproducts of each unit process for manufacturing the semiconductor devices and the corresponding processing fluid are discharged into the gas scrubber system 52 from the processing devices 30. The gas scrubber system 52 removes impurities from the byproducts and processing fluids.

The analyzing unit 204 is connected to the sampling pipes 202, which are in turn connected to the connection pipes 114. The connection pipes 114 connect the contamination control apparatuses 100 to the discharging duct 50. The analyzing unit 204 analyzes the mixture of the gases (which can include a contaminant) flowing through the sampling pipes 202. For example, the analyzing unit 204 can detect and analyze ionic contaminants, metallic contaminants and organic contaminants included in the mixture.

Although embodiments of the present invention are described with respect to the contamination control apparatuses 100 covering valves of the fluid supply system 32 in the utility zone 14, it should be understood that valves in the clean room 12 or in the processing device 30 may also be covered with the contamination control apparatus 100. In addition, the contamination control apparatus 100 may also cover the valves in exiting pipes 34 for connecting each of the processing devices 30 with the discharging duct 50, or may cover some or all of the valves fitting members used in the clean room system 10.

The cover 106, which shields various pipes or joint fitting members, may reduce the contaminant leaked therefrom that spreads over other regions of the clean room system 10. The leaked contaminant is discharged through the discharging duct 50 with the air supplied into the cavity 106c from the clean room 12 and the utility zone 14. The analyzing unit 204 analyzes the mixture of the leaked contaminant and the supplied gas. Accordingly, the air circulating through the clean room 12, the utility zone 14, the air circulation duct 18, and the ceiling chamber 16 may be sufficiently prevented from being contaminated, and the joint portions 104 such as the valves and fitting members may be more efficiently controlled.

With reference to FIG. 3, the analyzing unit 204 may be connected to the monitoring unit 206 for monitoring a contamination leakage from the joint portions 104 using analysis data produced thereby. As illustrated, the monitoring unit 206 includes a comparator 206a for comparing the analysis data on the contaminant with reference data, a signal generator 206b for generating a warning signal in accordance with the comparison result, and a display device 206c for displaying the analysis data. The analysis data can include, for example, a concentration of the contaminant in the mixture and/or an identification of various components of the contaminant. The monitoring unit 206 compares the analysis data with the reference data, and generates the warning signal based on the comparison. For example, the warning signal can be generated when the analysis data is less than or greater than a preset threshold amount defined by the reference data. The analysis data, including the comparison result, can be displayed in the display device 206c.

Figure 5:
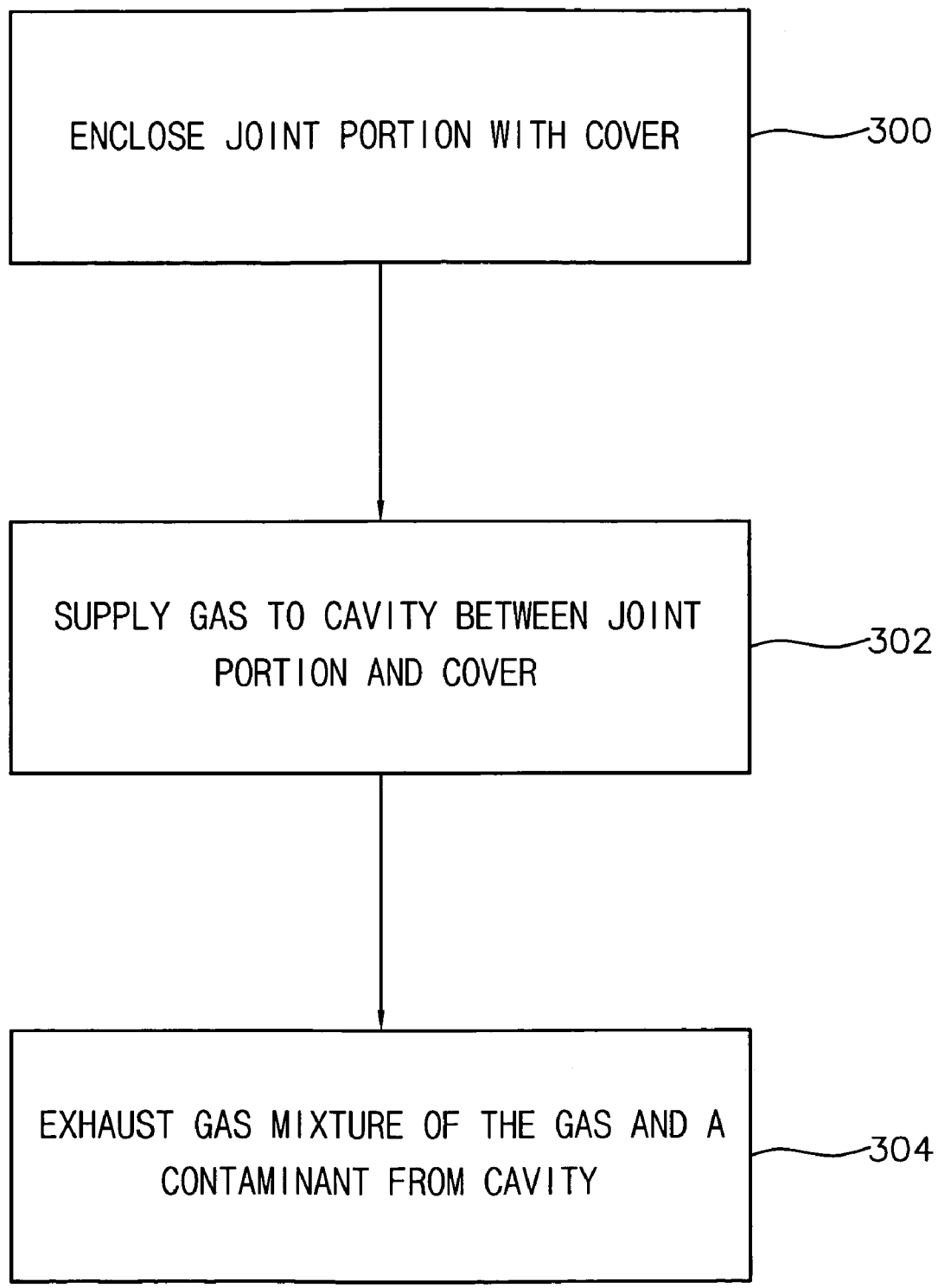
FIG. 5 is a flowchart illustrating operations according to embodiments of the present invention.

As illustrated in FIG. 5, a joint portion is enclosed with a cover (Block 300). The joint portion connects at least two pipes, such as the joint portion 104 illustrated in FIG. 1. The cover (such as the cover 106 in FIGS. 1 and 2) defines an enclosed cavity between the joint portion and the cover. A contaminant from the joint portion can be contained in the cavity. A gas is supplied to the cavity through an inlet port (Block 302). A gas mixture of the gas and the contaminant is exhausted from the cavity through an outlet port (Block 304). In some embodiments of the invention, the exhausted gas mixture is analyzed, for example to determine the concentration of the contaminant or the composition of the gas mixture.

According to embodiments of the present invention, the contamination control apparatus covers the joint portion connecting at least two pipes through which the processing fluid flows, so that the contaminant leaked from the joint portion may be substantially prevented from spreading over other regions of the clean room system. In addition, the leaked contaminant can be discharged through the discharging duct, and the concentration and/or components of the contaminant may be analyzed using the analyzing unit. The signal generator can generate a warning signal based on the comparison.

Accordingly, the processing devices, the clean room system and the semiconductor substrate may be substantially prevented from being contaminated by the leaked contaminant. The valves and/or fitting members installed on the pipes through which the processing fluid or the discharging gas flows can be controlled efficiently. The contaminant may be efficiently removed from the clean room through the discharging duct. In addition, the pipes through which the processing fluid flows and the valve for controlling the amount and pressure of the processing fluid may be easily repaired and the maintenance cost of the system may be reduced. Furthermore, the time during which the clean room system is not operated due to the leaked contaminant is reduced, so that the productivity of the semiconductor device may be improved.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

What is claimed is:

1. A contamination control apparatus for use with a joint portion that connects at least two pipes configured to allow a processing fluid to flow therethrough, the contamination control apparatus comprising:
    a cover configured to enclose the joint portion and to provide an enclosed cavity between the cover and the joint portion;
    an inlet port connected to the cover and configured to supply a gas to the cavity; and
    an outlet port connected to the cover and configured to exhaust the gas and a contaminant from the cavity.

2. The contamination control apparatus of claim 1, further comprising a plurality of ribs configured to support the cover.

3. The contamination control apparatus of claim 1, further comprising a filter connected to the inlet port and configured to filter the gas being supplied to the cavity.

4. The contamination control apparatus of claim 1, wherein the cover comprises a fluoropolymer.

5. The contamination control apparatus of claim 1, wherein the joint portion is installed between the pipes and includes at least one valve configured to control an amount and/or a pressure of the processing fluid flowing therethrough.

6. The contamination control apparatus of claim 1, wherein the cover comprises a slide zipper configured to open and/or close the cover.

7. The contamination control apparatus of claim 1, wherein the cover comprises a transparent window.

8. The contamination control apparatus of claim 1, further comprising a discharging duct connected to the outlet port and a connection pipe configured to connect the outlet port and the discharging duct.

9. A contamination control apparatus for use with a joint portion that connects at least two pipes configured to allow a processing fluid to flow therethrough, the contamination control apparatus comprising:
    a cover configured to enclose the joint portion and to provide an enclosed cavity between the cover and the joint portion;
    an inlet port connected to the cover and configured to supply a gas to the cavity;
    an outlet port connected to the cover and configured to exhaust the gas and a contaminant from the cavity; and
    a pair of sealing pads configured to seal the cover at end portions thereof.

10. The contamination control apparatus of claim 9, wherein the pads comprises a silicon-based material.

11. A contamination management system for use with a joint portion that connects at least two pipes configured to allow a processing fluid to flow therethrough, the contamination management system comprising:
    at least one control unit including: a cover configured to enclose the joint portion and providing an enclosed cavity between the cover and the joint portion; an inlet port connected to the cover and configured to supply a gas to the cavity; and an outlet port connected to the cover and configured to exhaust the gas and a contaminant from the cavity through a discharging duct;
    a plurality of sampling pipes connected to the outlet port and configured to sample the contaminant, the sampling pipes being connected to a connection pipe connecting the outlet port and the discharging duct; and
    an analyzing unit connected to the sampling pipes configured to analyze the sampled contaminant.

12. The contamination management system of claim 11, further comprising a monitor unit configured to monitor the contaminant from the joint portion using analysis data from the analyzing unit.

13. The contamination management system of claim 12, wherein the analysis data represents a concentration of the contaminant and/or components of the contaminant.

14. The contamination management system of claim 13, wherein the monitoring unit includes:
    a comparator configured to compare the analysis data of the contaminant with reference data;
    a signal generator configured to generate a warning signal based on a comparison between the analysis data of the contaminant and the reference data; and
    a display device for displaying the analysis data.

15. The contamination management system of claim 13, wherein the discharging duct is connected to a gas scrubber system configured to reduce the contaminant in a gas mixture discharged from the cover.

16. The contamination management system of claim 11, wherein the processing fluid includes a processing gas and/or a chemical for manufacturing a semiconductor device.

17. The contamination management system of claim 11, wherein the control unit comprises a plurality of ribs configured to support the cover.

18. The contamination management system of claim 11, wherein the control unit comprises a filter connected to the inlet port and configured to filter the gas being supplied to the cavity.

19. The contamination management system of claim 18, wherein the filter includes a high efficiency particulate air filter and/or an ultra low penetration air filter.

20. The contamination management system of claim 11, wherein the joint portion is installed between the pipes and includes at least one valve configured to control an amount and/or a pressure of the processing fluid.

21. The contamination management system of claim 11, further comprising a pair of sealing pads configured to seal the cover at end portions thereof.

22. The contamination management system of claim 11, wherein the cover comprises a slide zipper configured to open and/or close the cover.

23. A method for reducing contamination in a clean room, the method comprising:
    enclosing a joint portion connecting at least two pipes in a clean room with a cover that defines an enclosed cavity therebetween, wherein a contaminant from the joint portion is contained in the cavity;
    supplying a gas to the cavity through an inlet port;
    exhausting a gas mixture of the gas and the contaminant from the cavity through an outlet port.

24. The method of claim 23, further comprising analyzing the exhausted gas mixture.

25. A contamination control system comprising:
    at least two pipes connected by a joint portion and configured to allow a processing fluid to flow therethrough;
    a cover configured to enclose the joint portion and to provide an enclosed cavity between the cover and the joint portion;
    an inlet port connected to the cover and configured to supply a gas to the cavity; and
    an outlet port connected to the cover and configured to exhaust the gas and a contaminant from the cavity.

* * * * *